(12) United States Patent
Groenendaal et al.

(10) Patent No.: US 7,534,781 B2
(45) Date of Patent: *May 19, 2009

(54) CRYSTALLINE AMOXICILLIN TRIHYDRATE POWDER

(75) Inventors: Jan Willem Groenendaal, Delft (NL); Everardus Johannus Antonius Maria Leenderts, Rhoon (NL); Thomas Van Der Does, Wilnis (NL)

(73) Assignee: DSM IP Assets B.V., Heerlen (NL)

( * ) Notice: Subject to any disclaimer, the term of this patent is extended or adjusted under 35 U.S.C. 154(b) by 403 days.

This patent is subject to a terminal disclaimer.

(21) Appl. No.: 10/548,266

(22) PCT Filed: Mar. 19, 2004

(86) PCT No.: PCT/EP2004/002989

§ 371 (c)(1),
(2), (4) Date: Sep. 7, 2005

(87) PCT Pub. No.: WO2004/082661

PCT Pub. Date: Sep. 30, 2004

(65) Prior Publication Data

US 2006/0166958 A1    Jul. 27, 2006

Related U.S. Application Data

(60) Provisional application No. 60/456,188, filed on Mar. 21, 2003, provisional application No. 60/456,187, filed on Mar. 21, 2003.

(30) Foreign Application Priority Data

Mar. 21, 2003 (EP) .................................. 03100731
Mar. 21, 2003 (EP) .................................. 03100732

(51) Int. Cl.
*C07D 499/54* (2006.01)
*A61K 31/43* (2006.01)

(52) U.S. Cl. ........................................ 514/197; 540/335

(58) Field of Classification Search ................ 540/335; 514/197

See application file for complete search history.

(56) References Cited

U.S. PATENT DOCUMENTS

| | | | | |
|---|---|---|---|---|
| 5,998,610 A * | 12/1999 | Centellas et al. | ............ | 540/215 |
| 6,440,462 B1 * | 8/2002 | Raneburger et al. | ......... | 424/489 |
| 2002/0137926 A1 * | 9/2002 | Kosal et al. | ................. | 540/321 |
| 2006/0172987 A1 * | 8/2006 | Groenendaal et al. | ....... | 514/192 |

FOREIGN PATENT DOCUMENTS

| | | | |
|---|---|---|---|
| WO | WO 9417800 A1 * | 8/1994 | |
| WO | WO 97/33564 | 9/1997 | |
| WO | WO 99/11261 | 3/1999 | |
| WO | WO 9955710 A1 * | 11/1999 | |
| WO | WO 00/41478 | 7/2000 | |

OTHER PUBLICATIONS

International Search Report, May 27, 2004.

* cited by examiner

*Primary Examiner*—Mark L Berch
(74) *Attorney, Agent, or Firm*—Nixon & Vanderhye P.C.

(57) ABSTRACT

The invention relates to crystalline amoxicillin trihydrate powder having a bulk density higher than 0.45 g/ml. The invention also relates to a process for preparing crystalline amoxicillin trihydrate powder, said process comprising: crystallizing amoxicillin trihydrate from a solution containing dissolved amoxicillin; separating the crystals from said solution; and drying the separated crystals, resulting in crystalline powder having a bulk density higher than 0.45 g/ml.

35 Claims, No Drawings

CRYSTALLINE AMOXICILLIN TRIHYDRATE POWDER

This application is the US national phase of international application PCT/EP2004/002989 filed 19 Mar. 2004 which designated the U.S. and claims benefit of EP 03100732.1; EP 03100731.3; U.S. 60/456,188 and U.S. 60/456,187, all dated 21 Mar. 2003, the entire content of each of which is hereby incorporated by reference.

The present invention relates to crystalline amoxicillin trihydrate powder. The invention also relates to a process for preparing crystalline amoxicillin trihydrate powder.

Crystalline powder of a β-lactam antibiotic can be obtained by crystallizing the β-lactam antibiotic from a solution containing the β-lactam antibiotic in dissolved form, separating the crystals obtained, and drying the crystals. In the art, crystals of a β-lactam antibiotic are also referred to as powder.

The known powders have poor flow properties. The particle size is small, and the bulk density is low. This is for instance described in WO-A-9733564 disclosing for instance powder of amoxicillin trihydrate having an average volume-based grain size of 10 μm to 30 μm and a bulk density of 0.15 g/ml to 0.45 g/ml. Due to the poor flow properties of the known powder, the known powder as such is not suitable in applications requiring sufficient flow characteristics, such as for instance filling of capsules.

In order to improve the flow properties, the known powder can be subjected to processes referred to in the art as granulation, compacting, agglomeration, or aggregation to form larger particles having improved flow properties, said larger particles typically having a average volume-based grain size of greater than 100 μm, see for instance WO-A-9733564 and WO-A-9911261. The resulting larger particles having improved flow properties may for instance be used as a filling material for capsules or may be used for the preparation of tablets.

These processes require additional process steps, which is disadvantageous. Moreover, if not properly applied these processes may impair the properties of the antibiotic such as colour, stability. Moreover, we found that the dissolution rate of the resulting product is low.

Surprisingly we found crystalline amoxicillin trihydrate powder having a bulk density higher than 0.45 g/ml; and a process for the preparation thereof.

The crystalline powder according to the invention has improved flow properties, without having to be subjected to processes such as granulation, compacting, agglomeration or aggregation. If it would still be desired to subject the crystalline powder to processes such as granulation, compacting, agglomeration or aggregation, and the like, applying these processes is facilitated due to the improved flow properties of the crystalline powder according to the invention. Moreover, an increased quantity of crystalline powder can be fed into a capsule of a given size.

As used herein crystalline amoxicillin trihydrate powder, refers preferably to a product consisting mainly of crystals of amoxicillin trihydrate. It will be understood that crystals do not refer to aggregates formed by the build-up of crystals, for instance with the aid of a binding agent like water or starch paste, or mechanical force like roller compacting or extrusion. Some unintended formation of aggregates may occur during usual handling, for instance during drying. Aggregates can be seen using optical microscopy applied at a magnification of 140×. As used herein a product consisting mainly of crystals of the β-lactam antibiotic refers preferably to a product comprising at least 70 wt. % crystals of amoxicillin trihydrate, preferably at least 80 wt. %, more preferably at least 90 wt. %, more preferably at least 95 wt. %, more preferably at least 98 wt. %. These percentages can be determined using a combination of air jet sieving and optical microscopy. Air Jet sieving is advantageously carried out using an Alpine Air Jet 200LS-N air jet sieve during 1 minutes at 1200 Pa for a sample weight of 10 g). Optical microscopy is advantageously carried out by taking a sample of 5 mg, suspending the sample in 4 drops of paraffin oil on a surface on a surface area of 22×40 mm, and using a magnification of 140×.

It will be understood that the amoxicillin trihydrate may contain some impurities. The crystalline amoxicillin trihydrate powder according to the invention may for instance contain at least 90 wt. %, preferably at least 95 wt. %, more preferably at least 98 wt. % of amoxicillin trihydrate. These weight percentages are given relative to the weight of the crystalline powder. Preferably, the amoxicillin trihydrate powder is free of auxiliaries.

Preferably, the crystalline powder according to the invention has a bulk density higher than 0.46 g/ml, preferably higher than 0.5 g/ml, more preferably higher than 0.55 g/ml. This further improves the flow properties. Moreover, an increased bulk density is advantageous as crystalline powder may be fed into a certain volume, for instance a capsule. There is no specific upper limit for the bulk density. The bulk density may be less than 0.8 g/ml, for instance less than 0.7 g/ml. The bulk density is preferably determined according to USP 24, method I, (page 1913).

Preferably, the crystalline powder according to the invention has a tapped density higher than 0.6 g/ml, preferably higher than 0.7, more preferably higher than 0.8 g/ml. An increased tapped density improves the flow properties. Moreover, an increased tapped density is advantageous as more products may be fed into a certain volume, for instance a capsule. There is no specific upper limit for the tapped density. The tapped density may be less than 1.2 g/ml, for instance less than 1.1 g/ml, for instance less than 1.0 g/ml. The tapped density is preferably determined according to USP 24, method II, (page 1914).

The invention also relates to crystalline amoxicillin trihydrate powder, having a tapped density higher than 0.6 g/ml, preferably higher than 0.7, more preferably higher than 0.8 g/ml. This crystalline powder has improved flow properties compared to the known powder. The tapped density may be less than 1.2 g/ml, for instance less than 1.1 g/ml, for instance less than 1.0 g/ml.

Preferably, the crystalline powder according to the invention has a bulk density and tapped density such that the ratio $d_t/d_b$ is less than 1.7, preferably less than 1.6, preferably less than 1.5, preferably less than 1.45, wherein $d_t$=tapped density and $d_b$=bulk density. This results in improved flow ability. There is no specific lower limit for the ratio $d_t/d_b$. The ratio $d_t/d_b$ may be higher than 1.05, for instance higher than 1.1.

The invention also relates to crystalline amoxicillin trihydrate powder, having a bulk density and tapped density such that the ratio $d_t/d_b$ is less than 1.7, preferably less than 1.6, preferably less than 1.5, preferably less than 1.45. This crystalline powder has improved flow properties compared to the known powder. There is no specific upper limit for the ratio $d_t/d_b$. The ratio $d_t/d_b$ may be higher than 1.05, for instance higher than 1.1.

Preferably, the crystalline powder according to the invention has a bulk density and tapped density such that the compressibility index as defined by $((d_t-d_b)/d_t)*100\%$ is less than 40%, preferably less than 35%, more preferably less than 30%. This results in improved flow ability. There is no specific lower limit for the compressibility index. The compressibility index may for instance be higher than 10%.

The invention also relates to crystalline amoxicillin trihydrate powder having a bulk density and tapped density such that the compressibility index as defined by $((d_t-d_b)/d_t)*100\%$ is less than 40%, preferably less than 35%, more preferably less than 30%. This crystalline powder has improved flow properties compared to the known powder. There is no specific lower limit for the compressibility index. The compressibility index may for instance be higher than 10%.

The $d_{10}$ and $d_{50}$ are known ways for indicating a particle size distribution, $d_{50}$ referring to the value for the particle size such that 50 vol. % of the particles has a particle size smaller than said value. The $d_{50}$ is also referred to as average volume-based grain size. Likewise, $d_{10}$ refers to the value for the particle size such that 10 vol. % of the particles has a particle size smaller than said value. A preferred way for determining $d_{10}$ and $d_{50}$ is laser diffraction, preferably using Malvern equipment. A suitable apparatus for determining $d_{10}$ and $d_{50}$ is a Malvern particle sizer 2600 C obtainable from Malvern Instruments Ltd., Malvern UK, for instance using an objective of f=300 mm and a beam length of 14.30 mm. A polydisperse analysis model may advantageously be used.

We found that crystalline powder having improved flowability, bulk density and/or tapped density preferably have an increased $d_{50}$. The invention also provides crystalline amoxicillin trihydrate powder having a $d_{50}$ of higher than 10 μm, preferably higher than 20 μm, more preferably higher than 30 μm, more preferably higher than 35 μm, more preferably higher than 40 μm. There is no specific upper limit for the $d_{50}$. The $d_{50}$ of the crystalline powder according to the invention may be less than 150 μm, for instance less than 100 μm. The crystalline powder according to the invention preferably has increased $d_{10}$, preferably higher than 3 μm, preferably higher than 5 μm, more preferably higher than 8 μm, more preferably higher than 10 μm. There is no specific upper limit for the $d_{10}$ of the crystalline powder according to the invention. The $d_{10}$ of the crystalline powder according to the invention may be less than 50 μm.

The invention also provides a process comprising sieving the crystalline powder according to the invention. This allows the physical properties of the crystalline powder to be improved even further. Preferably, air jet sieving is applied.

The crystalline powder according to the invention can advantageously be used for the preparation of a pharmaceutical composition.

The crystalline powder according to the invention can advantageously be mixed with pharmaceutically acceptable auxiliaries and/or with a second pharmaceutically active agent. The crystalline powder according to the invention can for instance be mixed with between 0 and 50 wt. %, preferably between 0 and 40 wt. %, preferably between 0 and 30 wt. %, more preferably between 0 and 20 wt. %, preferably more than 1 wt. % of auxiliaries, relative to the sum weight of the crystalline powder and the auxiliaries. The crystalline powder according to the invention can for instance be mixed with clavulanic acid in salt form, preferably as a potassium salt, the weight ratio amoxicillin:clavulanic acid preferably being between 1:1 and 15:1, preferably between 2:1 and 10:1, preferably between 4:1 and 8:1. These weight ratios are calculated for the anhydrous amoxicillin and clavulanate in acid form. Therefore, the invention also relates to a mixture obtainable by a process comprising mixing the crystalline powder according to the invention with auxiliaries and/or a second pharmaceutically active agent. The invention also provides a mixture comprising (i) the crystalline powder according to the invention and (ii) auxiliaries and/or a second pharmaceutically active agent.

As a second pharmaceutically active agent, clavulanic acid in the form of a salt, preferably clavulanic acid in the form of a potassium salt is preferably used.

As auxiliaries may for instance be used fillers, dry binders, disintegrants, wetting agents, wet binders, lubricants, flow agents and the like. Examples of auxiliaries are lactose, starches, bentonite, calcium carbonate, mannitol, microcrystalline cellulos, polysorbate, sodium lauryl sulphate, carboymethylcelluslose Na, Sodium alginate, magnesium sterarate, silicon dioxid, talc.

Preferably, the mixture contains between 0 and 50 wt. %, preferably between 0 and 40 wt. %, preferably between 0 and 30 wt. %, more preferably between 0 and 20 wt. %, preferably more than 1 wt. % of auxiliaries. These weight percentages are given relative to the sum weight of the amoxicillin trihydrate and the auxiliaries.

Preferably the weight ratio amoxicillin:clavulanic acid is between 1:1 and 15:1, preferably between 2:1 and 10:1, preferably between 4:1 and 8:1. These weight ratios are calculated for the anhydrous amoxicillin and clavulanate in acid form.

The crystalline powder according to the invention can advantageously be used for filling a capsule for pharmaceutical use, for instance a gelatine capsule. Therefore, the invention also relates to a capsule containing the crystalline powder according to the invention or a capsule containing the mixture according to the invention. The crystalline powder according to the invention or the mixture according to the invention may be fed into a capsule in any suitable way. It will be understood by the skilled person that feeding material into a capsule may comprise forming a plug of the material, said plug being loosely comprised of the material. The skilled man will understand that a capsule containing crystalline powder or the mixture according to the invention also encompasses a capsule containing a plug of crystalline powder or a mixture according to the invention. The invention also relates to the use of the crystalline powder according to the invention or the mixture according to the invention for filling a capsule or for the preparation of a tablet.

The invention also relates to a process for filling a capsule, comprising feeding the crystalline powder according to the invention, optionally in combination with auxiliaries and/or a second pharmaceutically active agent, into the capsule. The invention also relates to a process comprising mixing the crystalline powder according to the invention with pharmaceutically acceptable auxiliaries, optionally together with a second pharmaceutically active agent, and feeding the resulting mixture into a capsule.

We found that the improved flow properties of the crystalline amoxicillin trihydrate powder according to the invention facilitate processes such as dry and wet granulation, agglomeration, tablet formation and the like. Therefore, the invention also provides a process comprising compressing the crystalline powder according to the invention or compressing the mixture according to the invention to produce compressed products. The compressed products may for instance be granules or tablets. The invention also relates to granules or tablets comprising the crystalline powder in compressed form or comprising the mixture according to the invention in compressed form.

The invention also relates to a process for preparing granules, comprising feeding the crystalline powder according to the invention or the mixture according to the invention, optionally in combination with auxiliaries and/or a second pharmaceutically active agent, to a roller compactor to produce compacts; and milling the compacts to produce granules. The granules produced may advantageously be sieved to obtain a desired particle size distribution. The invention also relates to granules obtainable by this process.

The invention also relates to a process for preparing granules, comprising mixing the crystalline powder according to the invention or the mixture according to the invention with a binding agent, the binding agent for instance being dissolved in a moistening liquid; compacting the crystals whilst moist or dry; granulating the compacts obtained through a sieve. The invention also relates to granules obtainable by this process.

The invention also relates to a process comprising forming a paste from the crystalline powder according to the invention or from the mixture according the invention; kneading the paste at a temperature of 10° C. to 80° C.; extruding the paste in a double-screwed extruder, and, if desired, drying the granules obtained. The invention also relates to granules obtainable this process.

The invention also relates to a process comprising compressing the granules according to the invention, optionally in mixture with auxiliaries and/or a pharmaceutically active agent to prepare tablets. The invention also relates to tablets obtainable by this process.

The invention also provides a process comprising mixing the crystalline amoxicillin trihydrate powder according to the invention, with amoxicillin in another physical form, preferably granules comprising amoxicillin trihydrate. The invention also provides a mixture comprising (i) amoxicillin trihydrate powder according to the invention and (ii) amoxicillin trihydrate in another physical form, preferably granules comprising amoxicillin trihydrate. In an embodiment, this mixture is auxiliary free. In an embodiment, this mixture comprises auxiliaries and/or a second pharmaceutically active agent. The granules comprising amoxicillin trihydrate in the mixture (to be mixed) may be any suitable granules, for instance having a $d_{50}$ of between 100 and 1000 µm. The $d_{50}$ of granules is preferably determined by making a sieve analysis. The granules may for instance comprise at least 90 wt. % of amoxicillin trihydrate, preferably at least 95 wt. %, more preferably at least 98 wt. % of amoxicillin trihydrate. Preferably, the granules are free of auxiliaries. The granules may be obtained by any suitable process wherein powder is combined to form granules, for instance by roller compacting, agglomeration, extrusion, aggregation, wet or dry granulation.

In one aspect of the invention, the crystalline powder according to the invention has a high dissolution rate. Preferably, the crystalline powder according to the invention has a $T_{85\%}$ of less than 55 minutes, preferably less than 50 minutes, preferably less than 40 minutes, preferably less than 30 minutes, preferably less than 25 minutes, preferably less than 20 minutes. $T_{85\%}$ may for instance be above 5 minutes. As used herein $T_{85\%}$ refers to period required to effect dissolution of 85 wt. % of a predetermined quantity (500 mg on an anhydrous basis) of the amoxicillin trihydrate in 900 ml water of 37° C. The determination of $T_{85\%}$ is preferably carried out under conditions as defined in USP 27, chapter "amoxicillin capsules", involving the use of apparatus 1 and applying a stirring rate of 100 rpm (USP 27, paragraph 711). Preferably, samples are taken at regular intervals, e.g. each 5 minutes, to determine the quantity of dissolved amoxicillin by UV absorption. Known products of amoxicillin trihydrate having a bulk density higher than 0.45 g/ml, for instance granules of amoxicillin trihydrate having a bulk density higher than 0.45 g/ml, are not found to have such high dissolution rates.

Therefore, the invention also relates to a product of amoxicillin trihydrate, said product having:
(i) a $T_{85\%}$ of less than 55 minutes, preferably less than 50 minutes, preferably less than 40 minutes, preferably less than 30 minutes, preferably less than 25 minutes; and
(ii) a bulk density higher than 0.45 g/ml, preferably higher than 0.5 g/ml, more preferably higher than 0.55 g/ml. There is no specific upper limit for the bulk density. The bulk density may be less than 0.8 g/ml, for instance less than 0.7 g/ml. $T_{85\%}$ may for instance be above 5 minutes.

The invention also relates to a product amoxicillin trihydrate, said product having
(i) a $T_{85\%}$ of less than 55 minutes, preferably less than 50 minutes, preferably less than 40 minutes, preferably less than 30 minutes, preferably less than 25 minutes; and
(ii) a tapped density higher than 0.6 g/ml, preferably higher than 0.7, more preferably higher than 0.8 g/ml. There is no specific upper limit for the tapped density. The tapped density may be less than 1.2 g/ml, for instance less than 1.1 g/ml, for instance less than 1.0 g/ml.

The invention also relates to a product of amoxicillin trihydrate, said product having:
(i) a $T_{85\%}$ of less than 55 minutes, preferably less than 50 minutes, preferably less than 40 minutes, preferably less than 30 minutes, preferably less than 25 minutes; and
(ii) a bulk density and tapped density such that the ratio $d_t/d_b$ is less than 1.7, preferably less than 1.6, preferably less than 1.5, preferably less than 1.45, wherein $d_t$=tapped density and $d_b$=bulk density. This results in improved flow ability. There is no specific lower limit for the ratio $d_t/d_b$. The ratio $d_t/d_b$ may be higher than 1.05, for instance higher than 1.1.

The invention also relates to amoxicillin trihydrate, said product having
(i) a $T_{85\%}$ of less than 55 minutes, preferably less than 50 minutes, preferably less than 40 minutes, preferably less than 30 minutes, preferably less than 25 minutes; and
(ii) a bulk density and tapped density such that the compressibility index as defined by $((d_t-d_b)/d_t)*100\%$ is less than 40%, preferably less than 35%, more preferably less than 30%. This results in improved flow ability. There is no specific lower limit for the compressibility index. The compressibility index may for instance be higher than 10%.

In a preferred embodiment, the product of amoxicillin trihydrate according to the invention has abovementioned preferred values for bulk density, tapped density, ratio $d_t/d_b$ and compressibility index mentioned above in combination.

The product of amoxicillin trihydrate according to the invention may be amoxicillin trihydrate in any suitable form. It will be understood that the product of amoxicillin trihydrate may still contain some impurities. Preferably, the product of amoxicillin trihydrate contains at least 90 wt. %, preferably at least 95 wt. %, more preferably at least 98 wt. % of amoxicillin trihydrate. These weight percentages are given relative to the weight of the product. Preferably, the product of amoxicillin trihydrate according to the invention is free of auxiliaries.

In one embodiment the product according to the invention is crystalline amoxicillin trihydrate powder according to the invention. In another embodiment embodiment the product according to the invention is a mixture comprising (i) amoxicillin trihydrate powder, preferably crystalline amoxicillin trihydrate powder according to the invention and (ii) amoxicillin trihydrate in another physical form, preferably granules comprising amoxicillin trihydrate.

The invention also provides a process comprising mixing amoxicillin trihydrate powder, preferably the crystalline amoxicillin trihydrate powder according to the invention, with amoxicillin in another physical form, preferably granules comprising amoxicillin trihydrate to obtain the product according to the invention. The quantities of amoxicillin trihydrate and granules to be mixed can be chosen such that preferred combinations of $T_{85\%}$ and the bulk density, tapped density, ratio $d_t/d_b$ and/or compressibility index are achieved. The amoxicillin trihydrate powder in the mixture (to be mixed) may be a powder having for instance a $d_{50}$ of between 1 and 100 μm. The crystalline amoxicillin trihydrate powder according to the invention is preferred.

The granules comprising amoxicillin trihydrate in the mixture (to be mixed) may be any suitable granules, for instance having a $d_{50}$ of between 100 and 1000 μm. The $d_{50}$ of the granules is preferably determined by making a sieve analysis. The granules may for instance comprise at least 90 wt. % of amoxicillin trihydrate, preferably at least 95 wt. %, more preferably at least 98 wt. % of amoxicillin trihydrate. Preferably, the granules are free of auxiliaries. The granules may be obtained by any suitable process wherein powder is combined to form granules, for instance by roller compacting, agglomeration, extrusion, aggregation, wet or dry granulation.

The product according to the invention can advantageously be used for the preparation of a pharmaceutical composition.

The product according to the invention can advantageously be mixed with pharmaceutically acceptable auxiliaries and/or with a second pharmaceutically active agent. The product according to the invention can for instance be mixed with between 0 and 50 wt. %, preferably between 0 and 40 wt. %, preferably between 0 and 30 wt. %, more preferably between 0 and 20 wt. %, preferably more than 1 wt. % of auxiliaries, relative to the sum weight of the product and the auxiliaries. The product according to the invention can for instance be mixed with clavulanic acid in salt form, preferably as a potassium salt, the weight ratio amoxicillin:clavulanic acid preferably being between 1:1 and 15:1, preferably between 2:1 and 10:1, preferably between 4:1 and 8:1. These weight ratios are calculated for the anhydrous amoxicillin and clavulanate in acid form. Therefore, the invention also relates to a mixture obtainable by a process comprising mixing the product according to the invention with auxiliaries and/or a second pharmaceutically active agent. The invention also provides a mixture comprising (i) the product according to the invention and (ii) auxiliaries and/or a second pharmaceutically active agent.

As a second pharmaceutically active agent, clavulanic acid in the form of a salt, preferably clavulanic acid in the form of a potassium salt is preferably used.

As auxiliaries may for instance be used fillers, dry binders, disintegrants, wetting agents, wet binders, lubricants, flow agents and the like. Examples of auxiliaries are lactose, starches, bentonite, calcium carbonate, mannitol, microcrystalline cellulos, polysorbate, sodium lauryl sulphate, carboymethylcelluslose Na, Sodium alginate, magnesium sterarate, silicon dioxid, talc.

Preferably, the mixture contains between 0 and 50 wt. %, preferably between 0 and 40 wt. %, preferably between 0 and 30 wt. %, more preferably between 0 and 20 wt. %, preferably more than 1 wt. % of auxiliaries. These weight percentages are given relative to the sum weight of the amoxicillin trihydrate and the auxiliaries.

Preferably the weight ratio amoxicillin:clavulanic acid is between 1:1 and 15:1, preferably between 2:1 and 10:1, preferably between 4:1 and 8:1. These weight ratios are calculated for the anhydrous amoxicillin and clavulanate in acid form.

The product according to the invention can advantageously be used for filling a capsule for pharmaceutical use, for instance a gelatine capsule. Therefore, the invention also relates to a capsule containing the product according to the invention or a capsule containing the mixture according to the invention. The product according to the invention or the mixture according to the invention may be fed into a capsule in any suitable way. It will be understood by the skilled person that feeding material into a capsule may comprise forming a plug of the material, said plug being loosely comprised of the material. The skilled man will understand that a capsule containing product or the mixture according to the invention also encompasses a capsule containing a plug of product or a mixture according to the invention. The invention also relates to the use of the product according to the invention or the mixture according to the invention for filling a capsule or for the preparation of a tablet.

The invention also relates to a process for filling a capsule, comprising feeding the product according to the invention, optionally in combination with auxiliaries and/or a second pharmaceutically active agent, into the capsule. The invention also relates to a process comprising mixing the product according to the invention with pharmaceutically acceptable auxiliaries, optionally together with a second pharmaceutically active agent, and feeding the resulting mixture into a capsule.

We found that the improved flow properties of the product according to the invention facilitate processes such as dry and wet granulation, agglomeration, tablet formation and the like. Therefore, the invention also provides a process comprising compressing the product according to the invention or compressing the mixture according to the invention to produce compressed products. The compressed products may for instance be granules or tablets. The invention also relates to granules or tablets comprising the product according to the invention in compressed form or the mixture according to the invention in compressed form.

The invention also relates to a process for preparing granules, comprising feeding the product according to the invention or the mixture according to the invention, optionally in combination with auxiliaries and/or a second pharmaceutically active agent, to a roller compactor to produce compacts; and milling the compacts to produce granules. The granules produced may advantageously be sieved to obtain a desired particle size distribution. The invention also relates to granules obtainable by this process.

The invention also relates to a process for preparing granules, comprising mixing the product according to the invention or the mixture according to the invention with a binding agent, the binding agent for instance being dissolved in a moistening liquid; compacting the crystals whilst moist or dry; granulating the compacts obtained through a sieve. The invention also relates to granules obtainable by this process.

The invention also relates to a process comprising forming a paste from the product according to the invention or from the mixture according the invention; kneading the paste at a temperature of 10° C. to 80° C.; extruding the paste in a double-screwed extruder, and, if desired, drying the granules obtained. The invention also relates to granules obtainable this process.

The invention also relates to a process comprising compressing the granules according to the invention, optionally in mixture with auxiliaries and/or a pharmaceutically active agent to prepare tablets. The invention also relates to tablets obtainable by this process.

Crystalline amoxicillin trihydrate powder may be obtained by preparing a solution comprising dissolved amoxicillin, crystallizing the amoxicillin trihydrate from said solution to form crystals, separating the crystals from said solution, and drying the separated crystals. As used herein the term crystalline powder includes, but is not limited to, the dried product obtained and/or obtainable by this process.

It was surprisingly found that crystalline powder having improved flow properties, in particular the high bulk density and/or high tapped density can be obtained by selecting the crystallizing, separation and/or drying conditions.

It was found that preparing crystalline powder having improved flow properties, in particular high bulk density and/or high tapped density, preferably includes carrying out the process, in particular the crystallizing, separating and drying, under such conditions that the dried crystals have an increased particle size, in particular increased $d_{50}$ and/or $d_{10}$.

Preferred crystallization conditions may include a relatively long residence time, relatively low concentrations of amoxicillin in the aqueous solution, relatively low concentrations of protein in the aqueous solution and/or using an aqueous solution having high purity. Further preferred conditions are described hereinafter.

It was further found that, in particular for crystals having an increased size, the extent of mechanical impact, for instance during crystallization, separation and/or drying influences the bulk density and tapped density. If the crystals are subjected to mechanical forces, for instance during drying and/or separating or transport of the crystals, the bulk density and tapped density are surprisingly found to increase compared to the situation where there is no mechanical impact. However, if the mechanical forces are too high, the bulk density and tapped density are found to decrease. Mechanical impact during separating can for instance be achieved during centrifuging. Mechanical impact during drying can for instance be achieved by using a contact dryer, for instance a Vrieco-Nauta contact dryer, or a flash dryer. Mechanical impact can also be achieved by applying pneumatic transport, for instance pneumatic transport of the amoxicillin trihydrate from the separation step to the drying step. Without wishing to be bound by any scientific theory, it is believed that a limited extent of mechanical impact has the effect that relatively large crystals having the shape of needles are broken, thereby resulting in an increase of the bulk density and/or tapped density. However, a too high extent of mechanical forces is believed to result in the production of crystals that are too fine, thereby reducing the bulk density and/or tapped density. Using this insight provided by the invention and by varying the mechanical forces the skilled man is able to find out the conditions where the optimal bulk density and/or tapped density are achieved.

Accordingly, the invention provides a process for preparing crystalline amoxicillin trihydrate powder, said process comprising: crystallizing the amoxicillin trihydrate from a solution containing dissolved amoxicillin; separating the crystals from said solution; drying the separated crystals; wherein the process, preferably the crystallizing, separating and/or drying, is carried out under such conditions that the resulting crystalline powder has a bulk density higher than 0.45 g/ml, preferably higher than 0.5 g/ml, more preferably higher than 0.55 g/ml. There is no specific upper limit for the bulk density. The process, preferably the crystallizing, separating and/or drying, may for instance be carried out under such conditions that the bulk density is less than 0.8 g/ml, for instance less than 0.7 g/ml.

The invention also provides a process for preparing crystalline amoxicillin trihydrate powder, said process comprising: crystallizing amoxicillin trihydrate from a solution containing dissolved amoxicillin; separating the crystals from said solution; drying the separated crystals; wherein the process, preferably the crystallizing, separating and/or drying, is carried out under such conditions that the resulting crystalline powder has a tapped density higher than 0.6 g/ml, preferably higher than 0.7 g/ml, more preferably higher than 0.8 g/ml. There is no specific upper limit for the tapped density. The process, preferably the crystallizing, separating and/or drying, may for instance be carried out under such conditions that the tapped density is less than 1.2 g/ml, for instance less than 1.1 g/ml, for instance less than 1.0 g/ml.

The invention also provides a process for preparing crystalline amoxicillin trihydrate powder, said process comprising: crystallizing amoxicillin trihydrate from a solution containing dissolved amoxicillin; separating the crystals from said solution; drying the separated crystals; wherein the process, preferably the crystallizing, separating and/or drying, is carried out under such conditions that the resulting crystalline powder has ratio $d_t/d_b$ of less than 1.7, preferably less than 1.6, preferably less than 1.5, preferably less than 1.45, wherein $d_t$=tapped density and $d_b$=bulk density. There is no specific lower limit for the ratio. The process, preferably the crystallizing, separating and/or drying, may for instance be carried out under such conditions that the ratio $d_t/d_b$ is higher than 1.05, for instance higher than 1.1.

The invention also provides a process for preparing crystalline amoxicillin trihydrate powder, said process comprising: crystallizing amoxicillin trihydrate from a solution containing dissolved amoxicillin; separating the crystals from said solution; drying the separated crystals; wherein the process, preferably the crystallizing, separating and/or drying, is carried out under such conditions that the compressibility index as defined by $((d_t-d_b)/d_t)*100\%$ is less than 40%, preferably less than 35%, more preferably less than 30%, wherein $d_t$=tapped density and $d_b$=bulk density. There is no specific lower limit for the compressibility index. The compressibility index may for instance be higher than 10%.

The invention also provides a process for preparing crystalline amoxicillin trihydrate powder, said process comprising: crystallizing amoxicillin trihydrate from a solution containing dissolved amoxicillin; separating the crystals from said solution; drying the separated crystals; wherein the process, preferably the crystallizing, separating and/or drying, is carried out under such conditions that the resulting crystalline powder has a $d_{50}$ of higher than 10 µm, preferably higher than 20 µm, more preferably higher than 30 µm, in particular higher than 35 µm, more preferably higher than 40 µm. There is no specific upper limit for the $d_{50}$. The process, preferably the crystallizing, separating and/or drying, may for instance be carried out under such conditions the $d_{50}$ of the resulting crystalline powder is less than 150 µm, for instance less than 100 µm. Preferably, the process, preferably the crystallizing, separating and/or drying, is carried out under such conditions that the dried crystals have a $d_{10}$ of higher than 3 µm, preferably higher than 5 µm, more preferably higher than 8 µm, more preferably higher than 10 µm. There is no specific upper limit for $d_{10}$. The process, preferably the crystallizing, separating and/or drying, may be carried out under such conditions that $d_{10}$ of the resulting crystalline powder is less than 50 µm.

The water activity that may be used to specify the extent to which a product is dried, may have any suitable value. Drying may be carried out such that the resulting crystalline amoxicillin trihydrate powder has a water activity of for instance higher than 0.05, for instance higher than 0.1, for instance higher than 0.15, for instance higher than 0.2, for instance higher than 0.25, for instance higher than 0.3, for instance less than 0.7, for instance less than 0.6, for instance less than 0.5. The water activity of the crystalline amoxicillin trihydrate powder according to the invention may for instance be higher than 0.05, for instance higher than 0.1, for instance higher than 0.15, for instance higher than 0.2, for instance higher than 0.25, for instance higher than 0.3. The water activity of the crystalline amoxicillin trihydrate powder according to the invention may for instance be less than 0.7, for instance less than 0.6, for instance less than 0.5. These values refer to the water activity measured at 25° C. The water activity is known to be defined as the equilibrium relative humidity divided by 100%. A preferred method for determining the water activity of a sample is to bring a quantity of the sample in a closed chamber having a relatively small volume, measuring the relative humidity as a function of time until the relative humidity has become constant (for instance after 30 minutes), the latter being the equilibrium relative humidity for that sample. Preferably, a Novasina TH200 Thermoconstanter is used, of which the sample holder has a volume of 12 ml and which is filled with 3 g. of sample.

Preferably, a process for preparing crystalline amoxicillin trihydrate powder according to the invention comprises preparing amoxicillin by reacting 6-amino-penicillanic acid or a salt thereof, with para-hydroxyphenyl glycine in activated form in the presence of an enzyme immobilized on a carrier; forming an aqueous solution containing the amoxicillin, said aqueous solution containing hydrochloric acid; and crystallizing the amoxicillin trihydrate from said aqueous solution.

Preferably, the solution from which the amoxicillin trihydrate is crystallized is an aqueous solution. Any suitable aqueous solution may be used. Suitable aqueous solutions include solutions wherein the weight ration water:organic solvent is between 100:0 and 70:30, preferably between 100:0 and 80:20, preferably between 100:0 and 90:10, preferably between 100:0 and 95:5, preferably between 100:0 and 99:1.

Preferably, the solution from which the amoxicillin trihydrate is crystallized contains less than 200 weight parts of protein per 1.000.000 weight parts of amoxicillin (total concentration of amoxicillin, whether or not in dissolved form), preferably less 100 weight parts of protein, more preferably less than 50 weight parts of protein, more preferably less than 35 weight parts of protein.

Preferably, the solution from which the amoxicillin trihydrate is crystallized is an aqueous solution having an amoxicillin concentration (total concentration of amoxicillin, whether or not in dissolved form) of less than 0.6 mol/l, preferably less than 0.5 mol/l, more preferably less than 0.4 mol/l, more preferably less than 0.3 mol/l.

The aqueous solution from which the amoxicillin trihydrate is crystallized, is preferably a solution containing hydrochloric acid or chloride. The aqueous solution from which the amoxicillin trihydrate is crystallized preferably contains between 0.9 and 5 mol of hydrochloric acid or chloride per mol amoxicillin (total concentration of amoxicillin, whether or not in dissolved form), preferably between 0.9 and 3 mol hydrochloric acid or chloride per mol amoxicillin, more preferably between 0.9 and 1.5 mol hydrochloric acid or chloride per mol amoxicillin. The aqueous solution from which the amoxicillin is crystallized preferably contains more than 1.0 mol of hydrochloric acid or chloride per mol of amoxicillin.

Preferably, the amoxicillin trihydrate is crystallized from an aqueous solution at a pH of between 2 and 7, preferably between 3 and 6. Preferably, the process comprises crystallizing amoxicillin trihydrate from the aqueous solution in a first step preferably at a pH of between 2 and 5, preferably between 3 and 4, and in a second step at a pH higher than in the first step, preferably between 4 and 7, preferably between 4.5 and 6.

Preferably, amoxicillin trihydrate is crystallized from the aqueous solution at a temperature of between 5° C. and 40° C., preferably between 10 and 30° C., more preferably between 15 and 25° C.

The solution from which the amoxicillin trihydrate is crystallized may be prepared in any suitable way. The aqueous solution containing dissolved amoxicillin may be prepared by dissolving amoxicillin trihydrate. It is possible to add amoxicillin trihydrate to a solution, and to effect dissolution of the added amoxicillin trihydrate. It is also possible to prepare an aqueous suspension by forming crystals of amoxicillin trihydrate in situ in a solution, and effecting dissolution of the crystals of amoxicillin trihydrate in said suspension. In a process for the preparation of amoxicillin, the process preferably comprises preparing an aqueous solution containing dissolved amoxicillin, said aqueous solution having an amoxicillin concentration of less than 0.6 mol/l, preferably less than 0.5 mol/l, more preferably less than 0.4 mol/l, more preferably less than 0.3 mol/l. The process preferably comprises preparing an aqueous solution containing dissolved amoxicillin, said aqueous solution having a pH of between 0 and 1.5, preferably between 0.5 and 1.2. Dissolving amoxicillin, may be carried out in any suitable way, for instance by adding an acid, preferably by adding hydrochloric acid to an aqueous suspension containing crystals of amoxicillin trihydrate. An acid, preferably hydrochloric acid, may be added in an amount of between 0.9 and 5 mol of hydrochloric acid per mol amoxicillin, preferably between 0.9 and 3 mol hydrochloric acid per mol amoxicillin, more preferably between 0.9 and 1.5 mol hydrochloric acid per mol amoxicillin. Preferably more than 1.0 mol of hydrochloric acid is added per mol of amoxicillin. In a preferred embodiment, the process comprises keeping the (aqueous) solution or (aqueous) suspension at a pH of less than 1.5, preferably less than 1.2, during a period of less than 60 minutes, preferably less than 30 minutes, more preferably less than 15 minutes, more preferably less than 10 minutes, more preferably less than 8 minutes, as this may improve the purity of the amoxicillin. Preferably, the process comprises mixing the aqueous solution or aqueous suspension with the acid using a fast mixer, for instance a static mixer. This can reduce the time during which the aqueous solution or suspension is kept low pH. Mixing of the acid with the aqueous suspension may be carried out at any suitable temperature, for instance higher than −5° C., for instance higher than 5° C., for instance higher than 10° C., for instance higher than 15° C., for instance less than 50° C., for instance less than 40° C. Preferably, the process comprises filtering the solution prior to said crystallizing. Preferably, the process comprises filtering the aqueous solution containing dissolved amoxicillin, said aqueous solution preferably having a pH of between 0 and 1.5, preferably between 0.5 and 1.2. The solution may be passed through any suitable filter. Preferably, a filter is used having a pore size of less than 40 μm, preferably less than 20 μm, preferably less than 10 μm, and more preferably less than 5 μm.

Amoxicillin trihydrate may advantageously be crystallized from said aqueous solution by increasing the pH, for instance by adding a base, for instance NaOH.

The crystallization may be carried out batch wise or continuously. When the process is carried out batch wise, addition of seed crystals to the aqueous solution is preferred. Preferably, the crystallization is carried out continuously.

Amoxicillin is preferably prepared by reacting 6-amino-penicilanic acid or derivatives thereof, for instance a salt of 6-amino-penicilanic acid, with an acylating agent selected from para-hydroxyphenyl glycine in activated form in the presence of an enzyme in an aqueous reaction medium. The para-hydroxyphenyl glycine in activated form is preferably an ester or amide of para-hydroxyphenyl glycine. Suitable esters include for instance 1 to 4 alkyl esters, for example methyl ester, ethyl ester, n-propyl or isopropyl esters. Glycol esters, for instance an ethylene glycol ester, may also be used. An amide that is unsubstituted in the —$CONH_2$ group may be used.

The enzyme may be any enzyme having hydrolytic activity (hydrolase). The enzyme may for instance be an acylase, inter alia Penicillin G acylase, amidase or esterase. Enzymes may be isolated from various naturally occurring microorganisms, for example fungi and bacteria. Organisms that have been found to produce penicillin acylase are, for example, *Acetobacter, Aeromonas, Alcaligenes, Aphanocladium, Bacillus* sp., *Cephalosporium, Escherichia, Flavobacterium, Kluyvera, Mycoplana, Protaminobacter, Pseudomonas* or *Xanthomonas* species.

Processes for the preparation of amoxicillin in the presence of an enzyme have been described in WO-A-9201061, WO-A-9417800, WO-A-9704086, WO-A-9820120, EP-A-771357, the contents of which are incorporated by reference.

The reaction may be carried out at any suitable pH, preferably at a pH of between 5 and 9, preferably between 5.5 and 8, more preferably between 6 and 7.5. The reaction may be carried out at any suitable temperature, for instance carried out at a temperature of between 0 and 40° C., preferably between 0 and 30° C., more preferably between 0 and 15° C.

The amoxicillin formed may be crystallized under the conditions at which the reaction is carried out. Crystallization of amoxicillin may for instance be effected at a pH of between 5 and 8, preferably between 5.5 and 7.5.

Preferably, the enzyme is an enzyme immobilized on a carrier. Any suitable carrier may be used. Preferably, the carrier comprises a gelling agent and a polymer containing free amino groups. Preferably, the polymer is selected from alginate amine, chitosan, pectin, or polyethylene imine. Preferably, the gelling agent is gelatin. This carrier and the preparation thereof are described in EP-A-222 462 and WO-A-9704086. Prior to immobilization, the isolated enzyme is preferably purified using ion exchange chromatography.

Preferably, the enzyme is an enzyme immobilized on a carrier, and the process preferably comprises separating a product comprising the amoxicillin formed from the immobilized enzyme. Said separating of the product from the immobilized enzyme may be carried out using any suitable method, for instance by using gravity or a screen that is not permeable to the major part of the immobilized enzyme. Preferably, the product separated from the immobilized enzyme contains less than 200 weight parts of protein per 1.000.000 weight parts of the amoxicillin, preferably less 100 weight parts of protein, more preferably less than 50 weight parts of protein, more preferably less than 35 weight parts of protein per 1.000.000 weight parts of the amoxicillin. This is preferably achieved by applying an enzyme sufficiently immobilized on a carrier to avoid separation of small amounts of protein from amoxicillin trihydrate. This has the advantage that the final amoxicillin trihydrate obtained contains less than 200 weight parts of protein per 1.000.000 weight parts of the amoxicillin, preferably less 100 weight parts of protein, more preferably less than 50 weight parts of protein, more preferably less than 35 weight parts of protein per 1.000.000 weight parts of amoxicillin. The product separated from the immobilized enzyme may be an aqueous solution containing amoxicillin in dissolved form. The product separated from the immobilized enzyme may also be a wet cake. The separated product is preferably an aqueous suspension comprising amoxicillin trihydrate crystals. Preferably, the process comprises dissolving said amoxicillin trihydrate crystals to form an aqueous solution containing dissolved amoxicillin.

The invention also relates to crystalline amoxicillin trihydrate powder obtainable by the process according to the invention.

The invention will be further elucidated by means of the following examples, without however being limited thereto.

EXAMPLES AND COMPARATIVE EXPERIMENT

Examples I-V

Preparation of Immobilized Enzyme

*Escherichia coli* penicillin acylase was isolated as described in WO-A-9212782, purified using ion exchange chromatography, and immobilized as described in EP-A-222462 and WO-A-9704086.

As definition of penicillin G acylase activity the following is used: one unit (U) corresponds to the amount of enzyme that hydrolyses per minute 1 µmole penicillin G under standard conditions (100 g.l$^{-1}$ Penicillin G potassium salt, 0.05 M potassium phosphate buffer, pH value 8.0, 28° C.).

Production of Amoxicillin 162.2 g of 6-APA (6-amino-penicillanic acid) and 184.8 g of HPGM (D(-)-p-hydroxyphenylglycine methyl ester) were suspended in 450 ml of water. The suspension was cooled to a temperature of 10° C. To this reaction mixture 32850 Units of immobilized penicillin acylase were added, and water was added to a final volume of 1500 ml. The mixture was stirred for 6 hours. During the reaction the pH increased to 6.9, and at the end of the reaction the pH had decreased to 6.2. To this mixture 750 ml of water was added, and the suspension was filtrated over a sieve (with a mesh of 100 micrometer) in 2 hours to separate off the immobilized enzyme. The suspension obtained containing the amoxicillin trihydrate crystals was cooled to 0° C. The suspension contained less than 50 ppm of protein relative to amoxicillin trihydrate (less than 50 weight parts of protein per 1.000.000 weight parts of amoxicillin trihydrate).

An aqueous suspension containing amoxicillin in water (100 g amoxicillin trihydrate per liter of suspension) as obtained above was mixed with a 32 wt. % HCl solution (at a temperature of 25° C.) using a static mixer such as to obtain a solution having a pH of 1. The residence time in the static mixer was 1.5 minutes. The acidic solution obtained is pumped through two filters, the first filter having pores of 40 µm, the second filter having pores of 4.5 µm. The residence time in the filters was about 3 minutes. The acidic filtered solution and is fed to a first stirred tank in which a pH of 3.7 is maintained by addition of 8 M NaOH solution. The temperature in the first tank is between 17 and 23° C. The residence time in the first tank is 45 minutes. The contents of the first tank are fed to a second stirred tank in which a pH of 5.0 is maintained by addition of a 8 M NaOH solution. The temperature in the second stirred tank is between 17 and 23° C. The residence time in the second stirred tank is 15 minutes. The contents of tank 2 fed to a third stirred tank in which the a temperature of 1 to 5° C. is maintained, the residence time in the third tank being more than 4 hours. The contents of the third stirred tank are fed to an inverted filter centrifuge such as to isolate the amoxicillin crystals, resulting in a wet cake containing 86 wt. % solid material. The wet cake was washed with water, pneumatically transported to a conical vacuum contact drier (Vrieco-Nauta), in which it was dried at a temperature of 30 to 40° C. and a pressure of 30 mbar during 7 hours.

Measurement of Particle Size Distribution, Bulk Density and Tapped Density.

The particle size distribution (including $d_{10}$ and $d_{50}$) of samples from the mixer was determined using a Malvern particle sizer 2600 C with objective f=300 mm, malvern sample measurement unit PS1 and a Malvern dry powder feeder PS 64. The beam length was 14.30 mm. A polydisperse analysis model was used.

The bulk density was determined according to USP 24, method I, (page 1913).

The tapped density was determined according to USP 24, method II, (page 1914).

Five different batches were prepared using the method described above. Table 1 shows the tapped density, bulk density, $d_{50}$, $d_{10}$ of the resulting crystals.

Example VI

The powder of example V was subjected to air jet sieving (200 LS-N air jet sieve manufactured by Hosakawa Alpine). Sieving was carried out using a 75 μm screen during 10 minutes. A few agglomerates formed during said sieving were removed from the overheads fraction (not passed through the sieve) tusing a vibrating sieve (425 μm), after which tapped density, bulk density, $d_{50}$, $d_{10}$ of the resulting crystals of the overheads fraction was determined. The results are indicated in table 1. This example shows that the compressibility and the Hausner ratio are further decreased. The resulting powder flows through Klein cup 8 mm.

TABLE 1

|  | Bulk dens. ($d_b$) (g/ml) | Tap. dens. ($d_t$) (g/ml) | $d_t/d_b$ | $d_b*(1/d_b - 1/d_t)$ *100% | $d_{50}$ (μm) | $d_{10}$ (μm) |
|---|---|---|---|---|---|---|
| Ex. I | 0.51 | 0.73 | 1.43 | 30% | 43.1 | 11.4 |
| Ex. II | 0.56 | 0.78 | 1.39 | 28% | 42.8 | 8.8 |
| Ex. III | 0.56 | 0.81 | 1.45 | 31% | 47.8 | 9.9 |
| Ex. IV | 0.54 | 0.81 | 1.50 | 33% | 37.0 | 7.0 |
| Ex. V | 0.58 | 0.79 | 1.36 | 26% | 61 | 19 |
| Ex. VI | 0.59 | 0.74 | 1.25 | 20% | 86 | 36 |
| Comp. A | 0.26 | 0.55 | 2.12 | 53% | 17 | 4.0 |
| Ref. B | 0.26 | 0.47 | 1.8 | 45% | 66.3 | 17.4 |

Comparative Experiment A

In a chemical process for the preparation of amoxicillin, a solution containing amoxicillin in dilute HCl and isopropanol was obtained. This solution was fed to a stirred tank. The pH was kept at 3.7 at a temperature of 20° C. Subsequently the pH was raised to 5.0 by adding NaOH. The resulting mixture is maintained in a vessel at 1 to 5° C. during 3 to 12 hours. The amoxicillin was separated using a centrifuge, and dried using a fluid bed dryer. Table 1 shows the tapped density, bulk density, $d_{50}$, $d_{10}$.

Reference Experiment B

Example I was repeated with the difference that a the drying was not carried out using the a conical vacuum contact drier (Vrieco Nauta), but using a drier wherein the material was not mechanically impacted (Ventilation stove). Drying was carried out at a temperature of 35° C. during 16 hours. The results are indicated in table 1. Comparison of examples I-IV with example B shows that the use of mechanical impact during drying results in an increased bulk density and tapped density.

Example VII

6 Gelatine capsules (size 0) were filled by hand with of crystalline amoxicillin trihydrate powder of example IV (500 mg on an anhydrous basis per capsule). No auxiliaries were added. Dissolution tests were applied using apparatus 1 under the conditions as described in USP 27 under paragraph "amoxicillin capsules", including a stirring rate of 100 rpm and a temperature of 37° C. Six beakers each containing 900 ml of water were used. Samples were taken each 5 minutes, and the quantity of dissolved amoxicillin were determined employing UV absorption at the wavelength of maximum absorbance at 272 nm.

84 wt. % of the amoxicillin was dissolved in 15 minutes.
90 wt. % of the amoxicillin was dissolved in 20 minutes.

Comparative Experiment C

Example VII was repeated using commercial granular auxiliary-free amoxicillin trihydrate granules obtained by roller compacting of amoxicillin trihydrate powder having the size distribution as indicated in table 3. After 60 minutes 82.0 wt. % of the amoxicillin was dissolved

Comparative Experiment D

Example VII was repeated using commercial granular auxiliary-free amoxicillin trihydrate having a different particle size distribution as indicated in table 3. The results are indicated in FIG. 1. After 60 minutes 84.4 wt. % of the amoxicillin was dissolved

TABLE 2

|  | <125 μm | 125-250 μm | 250-500 μm | 500-850 μm | 850-1000 μm | >1000 μm | Bulk density | Tapped density |
|---|---|---|---|---|---|---|---|---|
| Ex. C | 14.5 | 4.9 | 20.7 | 53.7 | 5.6 | 0 | 0.68 | 0.85 |
| Ex. D | 8.6 | 3.1 | 24.9 | 57.1 | 6.3 | 0.3 | 0.69 | 0.83 |

Example VIII 20 g of amoxicillin trihydrate crystalline powder according to the invention, 2 g of microcrystalline cellulose (Avicel® PH102) were weighed in a 200 ml container and mixed in a Turbula T2C blender for 5 minutes. 0.1 g of Magnesium stearate was added mixed for an additional 2 minutes.

Part of the mixture was transferred to a die with a diameter of 7 mm and a height of 2.3 cm, such that the die was completely filled. A punch was placed on top of the die and a pressure of 5 kg was applied during 5 seconds. The resulting empty space in the die was completely filled and a pressure of 5 kg was applied again. This procedure was repeated until no volume decrease was observed. Finally, the formed plug was released from the die in fed into an empty gelatine capsule body nr.0 Star-lock® of Capsugel. The composition of the formulation is as follows:

| | |
|---|---|
| Amoxicillin trihydrate crystalline powder | 570.1 mg (500 mg amoxicillin) |
| Microcrystalline cellulose | 57.1 mg |
| Magnesium stearate | 2.8 mg |
| Sum | 630.0 mg |

This example shows that the crystalline powder according to the invention can directly be used for filling capsules without compactation or granulation step in a specified quantity of 500 mg amoxicillin (calculated as amoxicillin anhydrate)

Example IX 297.5 g of amoxicillin trihydrate crystalline powder according to the invention, 88.5 g of microcrystalline cellulose (Avicel® PH200), 10 g of croscarmellose sodium (Ac- Di-Sol®), and 1 g of silicium dioxide colloidal (Aerosil® 200), are weighed in a 1000 ml container and mixed in a Turbula TC2 blender for 10 minutes, 3 g of magnesium stearate is added and mixed for an additional 2 min.

The mixture is transferred to a hopper of a Korsch® EKO excenter tablet press, and tablets are pressed with the following properties:

The composition of the formulation is as follows:

| | |
|---|---|
| Amoxicillin trihydrate crystalline powder | 581.7 mg (500 mg amoxicillin) |
| Microcrystalline cellulose | 190.3 mg |
| Croscarmellose sodium | 20 |
| Silicium dioxide colloidal | 2 |
| Magnesium stearate | 6 mg |
| | 800 mg |

The invention claimed is:

1. Crystalline amoxicillin trihydrate powder having a bulk density higher than 0.45 g/ml and a $d_{50}$ lower than 100 μm.

2. Crystalline powder according to claim 1, having a tapped density higher than 0.6 g/ml, wherein said tapped density is determined according to USP 24, method II.

3. Crystalline powder according to claim 1 or claim 2, having a $d_{50}$ higher than 10 μm.

4. Crystalline powder according to claim 1, having a $d_{10}$ higher than 3 μm.

5. Crystalline powder according to claim 1, having a $T_{85\%}<55$ minutes, wherein $T_{85\%}$ is the period required to effect dissolution of 85 wt. % of a predetermined quantity (500 mg on an anhydrous basis) of the amoxicillin trihydrate in 900 ml water of 37° C.

6. Mixture comprising
   (i) crystalline powder according to claim 1; and
   (ii) (a) granules comprising amoxicillin trihydrate; and/or
       (b) a second pharmaceutically active agent; and/or
       (c) auxiliaries,
   wherein said granules have a $d_{50}$ of between 100 and 1000 μm.

7. Product of amoxicillin trihydrate having
   (i) $T_{85\%}<55$ minutes,
   (ii) bulk density higher than 0.45 g/ml; and
   (iii) a $d_{50}$ lower than 100 μm
   wherein $T_{85\%}$ is the period required to effect dissolution of 85 wt. % of a predetermined quantity (500 mg on an anhydrous basis) of the amoxicillin trihydrate in 900 ml water of 37° C.

8. Product according to claim 7, comprising (i) amoxicillin trihydrate powder and (ii) granules comprising amoxicillin, wherein said granules have a $d_{50}$ of between 100 and 1000 μm.

9. A composition comprising (i) amoxicillin trihydrate powder and (ii) granules comprising amoxicillin, wherein said amoxicillin trihydrate powder is crystalline amoxicillin trihydrate powder according to claim 1, wherein said amoxicillin trihydrate power has
   (i) $T_{85\%}<55$ minutes;
   (ii) bulk density higher than 0.45 g/ml; and
   (iii) a $d_{50}$ lower than 100 μm
   wherein $T_{85\%}$ is the period required to effect dissolution of 85 wt. % of a predetermined quantity (500 mg on an anhydrous basis) of the amoxicillin trihydrate in 900 ml water of 37° C.; and
   wherein said granules have a $d_{50}$ of between 100 and 1000 μm.

10. Product according to claim 8, wherein said granules are free of auxiliaries.

11. Product according to claim 7, wherein said product is free of auxiliaries.

12. Mixture comprising
    (i) product according to claim 7 and
    (ii) auxiliaries and/or a second pharmaceutical active agent.

13. Mixture according to claim 12, said mixture having:
    (i) $T_{85\%}<60$ minutes; and
    (ii) bulk density higher than 0.45 g/ml.

14. Mixture according to claim 6, wherein said second pharmaceutical active agent is clavulanic acid in the form of a salt.

15. Mixture according to claim 6, wherein said granules are free of auxiliaries, and wherein said granules have a $d_{50}$ of between 100 and 1000 μm.

16. A method of preparing a capsule or a tablet comprising filling a capsule or forming a tablet with a material comprising a crystalline powder according to claim 1.

17. A method of preparing a capsule or a tablet comprising filling a capsule or forming a tablet with a material comprising a mixture according to claim 6.

18. A method of preparing a capsule or a tablet comprising filling a capsule or forming a tablet with a material comprising a product according to claim 7.

19. A method of preparing a capsule or a tablet comprising filling a capsule or forming a tablet with a material comprising a mixture according to claim 12.

20. A capsule comprising a crystalline powder according to claim 1.

21. A capsule comprising a mixture according to claim 6.

22. A capsule comprising a product according to claim 7.

23. A capsule comprising a mixture according to claim 12.

24. A process for producing a compressed product comprising compressing a crystalline powder according to claim 1.

25. A process for producing a compressed product comprising compressing a mixture according to claim 6.

26. A process for producing a compressed product comprising compressing a product according to claim 7.

27. A process for producing a compressed product comprising compressing a mixture according to claim 12.

28. Granules or tablets comprising a crystalline powder according to claim 1, wherein said granules have a $d_{50}$ of between 100 and 1000 μm.

29. Granules or tablets comprising a mixture according to claim 6.

30. Granules or tablets comprising a product according to claim 7, wherein said granules have a $d_{50}$ of between 100 and 1000 μm.

31. Granules or tablets comprising a mixture according to claim 12, wherein said granules have a $d_{50}$ of between 100 and 1000 μm.

32. A process for preparing a pharmaceutical composition comprising forming the composition with a material comprising a crystalline powder according to claim 1.

33. A process for preparing a pharmaceutical composition comprising forming the composition with a material comprising a mixture according to claim 6.

34. A process for preparing a pharmaceutical composition comprising forming the composition with a material comprising a product according to claim 7.

35. A process for preparing a pharmaceutical composition comprising forming the composition with a material comprising a mixture according to claim 12.

* * * * *